United States Patent [19]

Munavalli et al.

[11] Patent Number: 4,594,413

[45] Date of Patent: Jun. 10, 1986

[54] PREPARATION OF N,N'-METHYLENE-2,2'-AZOPYRIDOCYANINES

[75] Inventors: Shekhar Munavalli; Edward J. Poziomek, both of Bel Air, Md.

[73] Assignee: The United States of America as represented by the Secretary of the Army, Washington, D.C.

[21] Appl. No.: 765,286

[22] Filed: Aug. 13, 1985

[51] Int. Cl.[4] .................. C07D 251/72; C07D 471/14; C07D 487/14
[52] U.S. Cl. ..................................................... 544/180
[58] Field of Search ......................................... 544/180

[56] References Cited

U.S. PATENT DOCUMENTS 3,056,751  10/1962  Fierce et al. ..................... 544/180

OTHER PUBLICATIONS

Leubner, J. Org. Chem., vol. 38, 1098 (1973).
Leubner et al., Chemical Abstracts, vol. 70, entry 42494q (1969).

*Primary Examiner*—John M. Ford
*Attorney, Agent, or Firm*—Anthony T. Lane; Robert P. Gibson; Edward F. Costigan

[57] ABSTRACT

Disclosed is a one step process for reacting certain aminopyridines and pyrimidines with a methylene halide, preferably methylene iodide, at reflux for from about overnight to about 72 hours to obtain corresponding N,N'-methylene-2,2'-azopyridocyanines in good yields.

7 Claims, No Drawings

PREPARATION OF N,N'-METHYLENE-2,2'-AZOPYRIDOCYANINES

GOVERNMENT RIGHTS

The invention described herein may be manufactured, used and licensed by the Government for Governmental purposes without the payment to us of any royalties thereon.

BACKGROUND OF THE INVENTION

Substituted and unsubstituted N,N'-methylene-2,2'-azapyridocyanines have recently been the subject of interest because of the suggestion made by Liepins et al, Ing. Eng. Chem. Prod. Res. Develop. 90, 4011(1971) and Leubner, J. Org. Chem. 38, 1098(1973) that the coupling of the azapyridocyanine moiety to a conjugated polymer backbone might yield super conducting polymers. The compounds also exhibit fluorescence, even at room temperature, according to Leubner et al, Chem. Abst. 70, 42494q(1969); Ber. Bunsenges Phys. Chem. 72, 1133(1968).

Leubner, J. Org. Chem. 38, 1098(1973) obtained a 10% yield of N,N'-methylene-2,2'-azapyridocyanine iodide by reacting methylene iodide with di(2-pyridyl) amine.

There is therefore a need for a higher yielding, efficient process for producing substituted and unsubstituted N,N'-methylene-2,2'-azapyridocyanines.

BRIEF DESCRIPTION OF THE INVENTION

This invention relates to a one step process for producing substituted or unsubstituted N,N'-methylene-2,2'-azapyridocyanines represented by the formulas

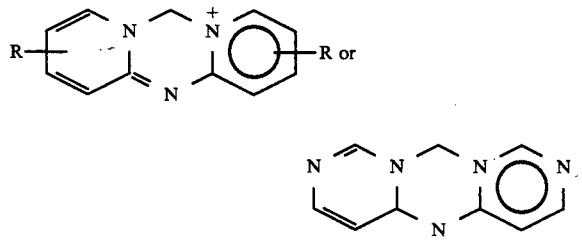

and halide quaternary salts thereof, wherein R is hydrogen or lower alkyl, by reaction of certain substituted or unsubstituted 2-amino-pyridines or pyrimidines with a methylene halide to obtain good yields.

DETAILED DESCRIPTION OF THE INVENTION

The present invention is based on the discovery that certain substituted and unsubstituted aminopyridines and a certain aminopyridine react with a methylene halide to obtain high yields of the corresponding N,N'-methylene-2,2'-azapyridocyanine according to the following reaction schemes.

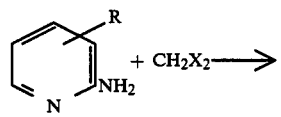

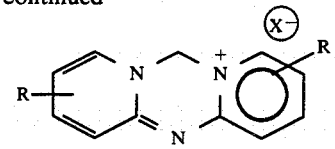

wherein R is hydrogen or lower alkyl and X is halogen, with the proviso that R at the 6-position of the aminopyridine must always be hydrogen.

Reaction Scheme A is generally carried out using equimolar amounts of the reactants, however, when R is hydrogen and the ratio of 2-aminopyridine to the methylene halide is increased to 1:2 and the reaction period is extended to about 72 hours, yields increase to more than 80%. The reaction in the presence of a dry, inert organic solvent, preferably dry acetonitrile, at reflux for from overnight (about 8–12 hours) to about 72 hours.

The reaction appears to be sensitive to the nature of the substituents on the pyridine ring and the size of the ring system. When attempts were made to react 3-nitro-2-aminopyridine or 3-aminopyrazole with methylene iodide, no reaction occurred as evidenced by the fact that only the starting materials were recovered from the reaction mixture. Although we do not intend to be bound by any theory of the reaction, it appears that the electron-withdrawing $NO_2$ group reduces via resonance, the nucleophilicity of the ring nitrogen and the exocyclic amino group. Thus, the reduced electron density of the ring nitrogen might be preventing the bis-alkylation of the pyridine nitrogen which is necessary for formation of the desired compounds. The method therefore does not appear applicable to 2-aminopyridines with electron withdrawing substituents. Electron dontating groups, such as lower alkyls, e.g. methyl, facilitate the reaction, whereas generally electron withdrawing groups on the pyridine ring results in failure of the reaction. In addition, the reaction appears to be highly susceptible to steric factors. This is demonstrated by the failure to obtain the expected product from 2-amino-6-methyl-pyridine(2-amino-6-picoline).

The process of this invention is also applicable to the reaction of 4-aminopyrimidine and methylene halide, e.g. methylene iodide, as shown in the following reaction scheme.

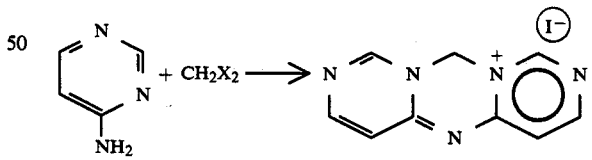

Reaction Scheme B is carried out at reflux in a dry, inert organic solvent, e.g. dry acetonitrile, for about 12 to 24 hours. Equimolar amounts of the reactants are used.

Reactions using 2-aminopyrimidine and 2-aminopyrazine were not successful. Thus, of the heterocycles analogous to pyridine, only the 4-aminopyrimidine reactant is suitable for the process of this invention.

As used herein in the specification and claims, "lower alkyl" means a straight chain alkyl of from 1 to 6 carbon atoms, methyl is preferred for use in the process of this invention; "halogen" means fluorine, chlorine, bromine or iodine, with iodine the preferred halogen. "Inert organic solvent" means a solvent inert to the reactants under the reaction conditions. The preferred solvent is dry, i.e. essentially water free acetonitrile.

The advantages of the one step process of this invention other than the fact it can be carried out in one step are the higher product yield of about 20% to 30+% as compared to the prior art 10% yield from di-(2-pyridyl)amine as well as the ready commercial availability of the starting materials.

The following examples illustrate the process of this invention. The structures of the compounds were established by analytical data and the NMR and UV spectra. All melting points are uncorrected and were taken with a Thomas Hoover capillary melting point apparatus. The NMR spectra were obtained on a Varian EM-390 spectrometer in $D_2O$ at the probe temperature(34° C.). The chemical shifts were relative to the interval standard TSP(sodium 3-trimethylsilylpropionate). All signals were downfield from the reference and the values were obtained by direct measurement on 10 ppm sweep-width. The UV data were obtained with a Cary 17 spectrophotometer.

EXAMPLE 1

N,N'-Methylene-2,2'-Azapyridocyanine (a) A mixture of 0.94 g(0.01 mole) of 2-aminopyridine and 2.67 g (0.01 mole) of methylene iodide in 25 ml. dry acetonitrile was refluxed for 20 hours when a solid golden material appeared. The reaction mixture was allowed to cool to room temperature and then filtered to give 0.326 g of the golden flakey material, m.p. 258°–260° C. An additional amount of 0.164 g of the product was obtained on concentration of the filtrate and trituration of the residue with acetone. The total yield was 32%. The yield dropped to 24% when 0.02 mole of the amine was used. This also necessitated a 28 hour reaction time. NMR: two multiplets ($\delta$=8.00 ppm, 4H, $\delta$=7.2 ppm, 4H) a singlet ($\delta$=6.35 ppm, H). UV max. 400, 300, 272, 223 (sh) nm, $H_2O$.

(b) On refluxing a mixture of 0.94 g (0.01 mole) of 2-aminopyridine and 5.34 g (0.02 mole) of methylene iodide in 30 ml dry acetone for 72 hours, a yellowish colored solid precipitated. The solvent was evaporated under reduced pressure. The residue was triturated with excess of ether, filtered and the precipitate was successively washed with excess of ether and acetone and the residue dried to give 1.277 g of the title compound in 81% yield.

EXAMPLE 2

N,N'-Methylene-3,3'-dimethyl-2,2'-azapyridocyanine

A solution of 1.08 g (0.01 mole) of 2-amino-3-picoline and 2.68 g (0.01 mole) of methylene iodide in 25 ml dry acetonitrile was refluxed for 28 hours. The solvent was evaporated under reduced pressure. The resulting viscous residue was dissolved in ethanol and the title compound was precipitated as a bright yellow solid by the addition of dry ether in a yield of 21% (0.341 g), m.p. 214° C.–216° C. The integral and NMR spectrum were consistent with the proposed structure: a singlet, 6H, —(CH$_3$)$_2$ $\delta$=2.5 ppm; a singlet, 2H, —CH$_2$— $\delta$=6.2 ppm; a triplet, 2H, (beta protons), $\delta$=7.2 ppm; a triplet, 4H (alpha and gamma protons), delta=7.9 ppm. UV: 406, 316, 273, 227 sh. and 205 sh. ($H_2O$).

EXAMPLE 3

N,N'-Methylene-4,4'-dimethyl-2,2'-azapyridocyanine

A mixture of 1.08 g (0.01 mole) of 2-amino-4-picoline and 2.68 g (0.01 mole) of methylene iodide in 25 ml dry acetonitrile was refluxed for 48 hours. The solvent was removed under reduced pressure. The residue was treated with ether, the ethereal solution was decanted off and the residue on triturating with dry alcohol yielded 0.41 g of the title product as a golden solid. The solid was repeatedly washed with ether and acetone, m.p. 238°–236° C. The NMR spectrum was consistent with the structure; a singlet 6H, —(CH$_3$)$_2$—, delta=2.45 ppm; a singlet, 2H, —CH$_2$—, delta=6.18 ppm; a doublet, 2H, two isolated Hs, delta=7.01; a doublet, 2H, beta-protons delta=7.08 ppm; a doublet, 2H, alpha Hs, delta=7.80 ppm.

EXAMPLE 4

N,N'-Methylene-5,5'-dimethyl-2,2'-azapyridocyanine

A solution of 1.08 g (0.01 mole) of 2-amino-5-picoline and 2.68 g (0.01 mole) of methylene iodide in 25 ml of dry acetone was refluxed overnight. The resulting precipitated yellow solid was filtered and washed repeatedly with acetone to yield 0.425 g of the title compound as a golden yellow crystalline material. A second crop of 0.1 g was obtained from the mother liquor, m.p. 256°–259° C. The NMR spectrum was consistent with the proposed structure; a singlet, 6H, —(CH$_3$)$_2$—, delta=2.30 ppm; a singlet, —CH$_2$—, delta 6.30 ppm; a doublet, 2H, protons beta to CH$_3$, delta=7.12 ppm, J=9 Hz; a doublet, 2H, protons, delta=7.74 ppm, J=2.1 Hz; a pair of doublets, 2H, delta=7.89 ppm, J=2.7 Hz, J=9.0 Hz.

EXAMPLE 5

N,N'-Methylene-5,5'-diaza-2,2'-azapyridocyanine

A solution of 0.48 g (0.005 mole) of 4-aminopyrimidine and 1.34 g (0.005 mole) of methylene iodide in 25 ml dry acetonitrile was refluxed for 20 hours. On cooling, a solid material precipitated. This solid was filtered and washed with acetone to give 0.0458 g of the title compound as a copper-red colored material, m.p. 254°–256° C. (decomposed). Recrystallization from dilute ethanol raised the m.p. to 273°–277° C. The NMR was consistent with the proposed structure; a singlet, —CH$_2$—, delta=6.25 ppm; a doublet, 2H, delta=6.8 ppm; a doublet of doublet, 2H, delta=8.2 ppm; a doublet, 2H, delta=8.8 ppm.

We claim:

1. A process for producing N,N'-methylene-2,2'-azapyridocyanines represented by the formulas

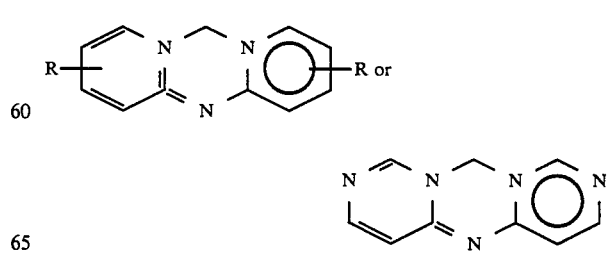

or the halide quaternary salts thereof, which comprises reacting a compound represented by the formulas

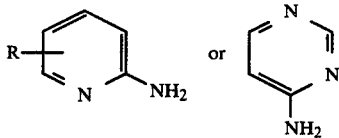

wherein R is hydrogen or lower alkyl, with the proviso that R at the 6-position of the aminopyridine must be hydrogen, with a methylene halide represented by the formula $CH_2X_2$ wherein X is halogen, under reflux in the presence of a dry, inert organic solvent for a time sufficient to complete the reaction.

2. The process of claim 1 wherein X is iodine and the solvent is acetonitrile.

3. The process of claim 2 wherein the reactants are 2-aminopyridine and methyl iodide and the product is N,N'-methylene-2,2'-azapyridocyanine.

4. The process of claim 2 wherein the reactants are 2-amino-3-picoline and methylene iodide and the product is N,N'-methylene-3,3'-dimethyl-2,2'-azapyridocyanine.

5. The process of claim 2 wherein the reactants are 2-amino-4-picoline and methylene iodide and the product is N,N'-methylene-4,4'-dimethyl-2,2'-azapyridocyanine.

6. The process of claim 2 wherein the reactants are 2-amino-5-picoline and methylene iodide and the product is N,N'-methylene-5,5'-dimethyl-2,2'-azapyridocyanine.

7. The process of claim 2 wherein the reactants are 4-aminopyrimidine and methylene iodide and the product is N,N'-methylene-5,5'-diaza-2,2'-azapyridocyanine.

* * * * *